(12) United States Patent
Haskell

(10) Patent No.: US 7,410,661 B2
(45) Date of Patent: *Aug. 12, 2008

(54) ENHANCED WOUND HEALING METHOD, PRODUCT AND COMPOSITION

(76) Inventor: Weston Haskell, P.O. Box 671, Fulshear, TX (US) 77441

( * ) Notice: Subject to any disclaimer, the term of this patent is extended or adjusted under 35 U.S.C. 154(b) by 5 days.

This patent is subject to a terminal disclaimer.

(21) Appl. No.: 11/377,805

(22) Filed: Mar. 16, 2006

(65) Prior Publication Data

US 2006/0159789 A1 Jul. 20, 2006

(51) Int. Cl.
*A61K 36/00* (2006.01)

(52) U.S. Cl. ...................... 424/769; 424/776

(58) Field of Classification Search ........ None
See application file for complete search history.

(56) References Cited

U.S. PATENT DOCUMENTS

| | | | |
|---|---|---|---|
| 4,035,483 A | | 7/1977 | Bnyan |
| 4,200,723 A | * | 4/1980 | Chen .................. 528/1 |
| 4,857,326 A | | 8/1989 | Stitt |
| 5,843,987 A | | 12/1998 | Rajagopalan et al. |
| 5,855,922 A | | 1/1999 | Danner |
| 6,033,573 A | | 3/2000 | Toles et al. |
| 6,060,101 A | | 5/2000 | Erasmus et al. |
| 6,165,539 A | | 12/2000 | Erasmus et al. |
| 6,271,214 B1 | | 8/2001 | Qiu |
| 6,296,838 B1 | * | 10/2001 | Bindra et al. ............. 424/61 |
| 6,461,599 B1 | * | 10/2002 | Ruben ..................... 424/73 |
| 6,727,211 B1 | * | 4/2004 | Aronson et al. ........... 510/146 |
| 7,052,723 B1 | * | 5/2006 | Tierra .................... 424/771 |
| 7,175,860 B2 | * | 2/2007 | Haskell .................. 424/769 |
| 2001/0022980 A1 | | 9/2001 | Bell et al. |
| 2003/0104075 A1 | | 6/2003 | Chevaux et al. |
| 2004/0039353 A1 | * | 2/2004 | Koenig et al. ............. 604/289 |
| 2004/0067224 A1 | | 4/2004 | Ernest |

FOREIGN PATENT DOCUMENTS

| | | | |
|---|---|---|---|
| DE | 2107641 | * | 2/1972 |
| DE | 3637826 | * | 5/1988 |
| RU | 2014823 | * | 6/1994 |

OTHER PUBLICATIONS

Wikipedia website publication entitled "Juglandaceae", at http://en.wikipeida.org/wiki/Juglandaceae, 2 pages—downloaded from internet on Apr. 23, 2007.*
http://www.fungusfocus.com/html/black_walnut.htm; pp. 1-3, 2003 (copyright).
http://www.uga.edu/fruit/walnut.htm; pp. 1-11, downloaded May 9, 2006.
http://www.wvu.edu/~agexten/hortcult/fruits/blkwalnt.htm: pp. 1-3, downloaded May 9, 2006.
Potts, Pathogenic bacteria attach to human fibronectin through a tandem beta-zipper, Nature, vol. 423, pp. 177-181 (May 3, 2003) (Abstract).
Berendt, Bacterial fibronectin-binding proteins and endothelial cell surface fibronectin mediate adherence of . . . , Microbiology, vol. 145, pp. 3477-3486 (1999).

* cited by examiner

*Primary Examiner*—Christopher R. Tate
(74) *Attorney, Agent, or Firm*—Bracewell & Giuliani LLP

(57) ABSTRACT

A method of obtaining a pathogen shield from nut husks where the composition is useful in promoting the wound healing. The method includes collecting nut husks, extracting fluid resident in the husks, and storing the collected fluid. The extraction process is conducted in an inert environment thereby preventing oxidation of the fluid. After collection, the expressed fluid can be transferred to storage prior to use, such as in metal-foil packets or glass ampoules.

4 Claims, 3 Drawing Sheets

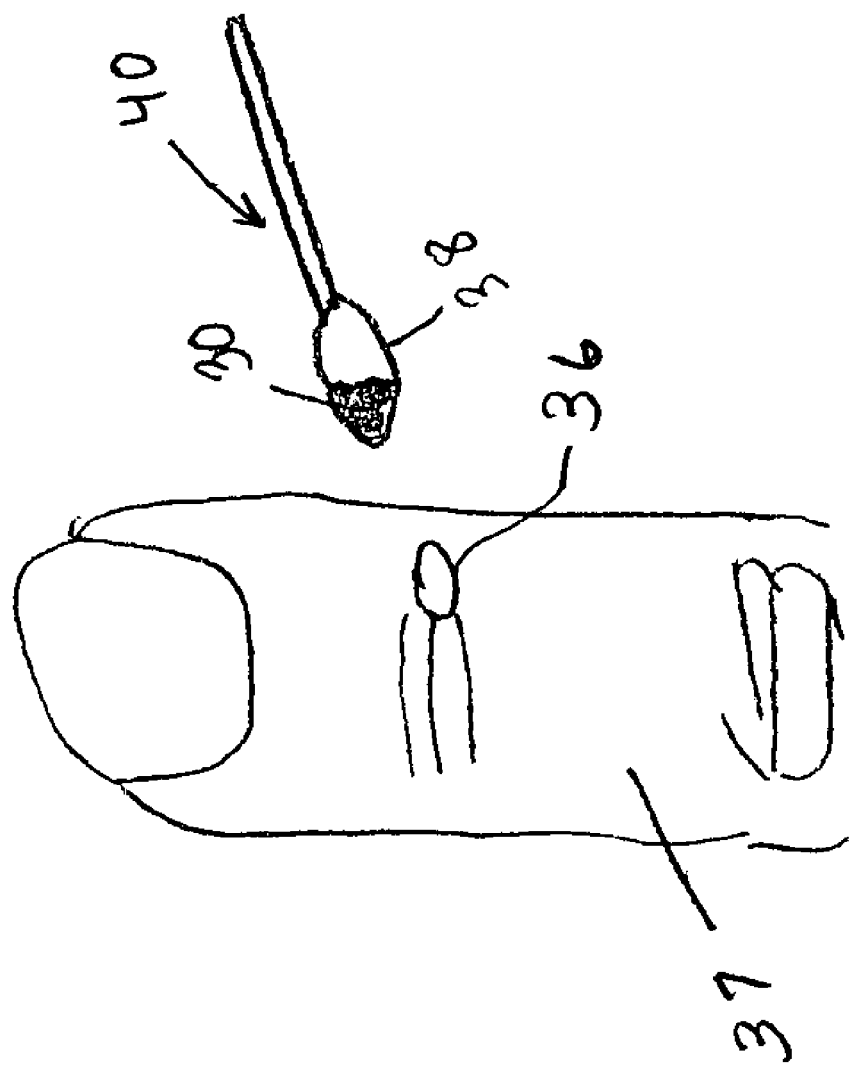

ENHANCED WOUND HEALING METHOD, PRODUCT AND COMPOSITION

RELATED APPLICATIONS

This application claims priority from U.S. application Ser. No. 10/909,481, filed Aug. 2, 2004 now U.S. Pat. No. 7,175,860, the full disclosure of which is hereby incorporated by reference herein.

FIELD OF THE INVENTION

The invention relates generally to a natural antiseptic and prophylactic agent. The invention also relates to methods, products and composition useful for healing wounds. The invention further relates to a process of collecting, storing, and applying the composition, where the process maintains the composition within an inert environment thereby preventing degradation of the composition.

DESCRIPTION OF RELATED ART

Many methods and compositions exist for promoting the speed of wound healing. These include ensuring the wound is cleaned as soon as possible to remove bacterial or septic agents that might cause the wound to become infected. Other methods involve isolating the wounded area within an oxygen rich environment to enhance the healing process. Compositions for aiding in wound healing include a myriad of antiseptic compounds, antibacterial agents, and others such as polysaccharides. Examples of these and other methods and compositions can be found in the following references: U.S. Pat. No. 6,271,214, U.S. Pat. No. 4,035,483, and U.S. Pat. No. 5,855,922.

However, the methods taught in each of the aforementioned references suffer from the drawback that the operative composition attacks or reacts with pathogens in the region where the composition is applied. Thus, once the anti-pathogen effect of the composition expires, the wound can become invaded and thus infected from later arriving pathogens. It is known that pathogenic bacteria attach and invade skin cells via a specific local mechanism, as discussed by Potts (Jennifer R. Potts, et al., Nature 423, 177-181 (2003). "Pathogenic bacteria attach to human fibronectin through a tandem beta-zipper") and Berendt (Berendt, A. R., et al., Microbiology 145, 3477-3486(1999) "Bacterial fibronectin-binding proteins and endothelial cell surface fibronectin mediate adherence of *Staphylococcus aureus* to resting human endothelial cells.") Thus a risk of infection is present if the wound is left unprotected at a time when pathogens come into contact with the wound.

Therefore, a need exists for a composition, product and a method of making the composition, where the composition can be applied to a wound and protect the wound from pathogen infection.

BRIEF SUMMARY OF THE INVENTION

The method herein described includes obtaining a pathogen shield by collecting nuts of the Juglandaceae Of this family only black walnut, *Carya nigra* and pecan *Carya illinoensis* produce shucks that when green contain the precursor to tannic acids—the active component which provides long term protection. The method further includes removing the green husks from the nuts. The husk removal step can be conducted in air if a soft brush in utilized in the shuck-brush machine. Extracting the pathogen shield fluid from these husks must be performed in an inert gas environment. That is an environment that is substantially oxygen free. The extraction of the fluid from the husk can be performed by pressing the husks under high pressure or a fluid extraction process using a solvent to extract resident fluids from the husks. The husks can come from nuts including pecans *Carya illinoensis*, and black walnuts *Juglans nigra*.

BRIEF DESCRIPTION OF THE SEVERAL VIEWS OF THE DRAWING

FIG. 5 illustrates application of the liquid extract onto a wound.

DETAILED DESCRIPTION OF THE INVENTION

While it had been known that the husks of certain nuts, such as from black walnuts, pecans, and others in this family of nuts, contained compounds that possessed antiseptic like qualities. It was not known that the presence of oxygen could oxidize these compounds and eliminate their prophylactic qualities. It was also believed that the compounds having these qualities included juglone and possibly tannic acid.

One of the discoveries with this invention is that tannic acid is possibly a product produced by oxidation of compounds naturally occurring within nut husks of this family, where these naturally occurring compounds are actually precursors via oxidation to tannic acid. These precursors to tannic acid exist in addition to juglone. Thus subjecting the nut husk extract to the oxygen in ambient air results in oxidation. This alters the characteristics of the extract and negates some of the antiseptic qualities while completely nullifying the prophylactic qualities of the extract. However it has been discovered that if the naturally occurring fluid within a nut husk, or the husk of nut similar to a pecan such as a black walnut, was extracted in an inert environment substantially void of oxygen; this elixir from the husk or any similar fluids, can be preserved for use long after the fluid was extracted from the husk.

Juglandaceae is one family of nut species considered for use with the present method. Pecans, hickory nuts, walnuts and black walnuts, among others, belong to the Juglandaceae family. Pecans can also be referred to as Juglans pecan, Juglans illinoensis, Hicoria pecan, *Carya illinoinensis*, and Carya pecan. Hickory can be known as Carya and walnut is sometimes referred to as Juglans. Black Hickory is known as *Carya texana Buck*. Many husks of these aforementioned nuts will stain the skin. Green husks from Black Hickory were found not to stain the skin.

Figure 1:
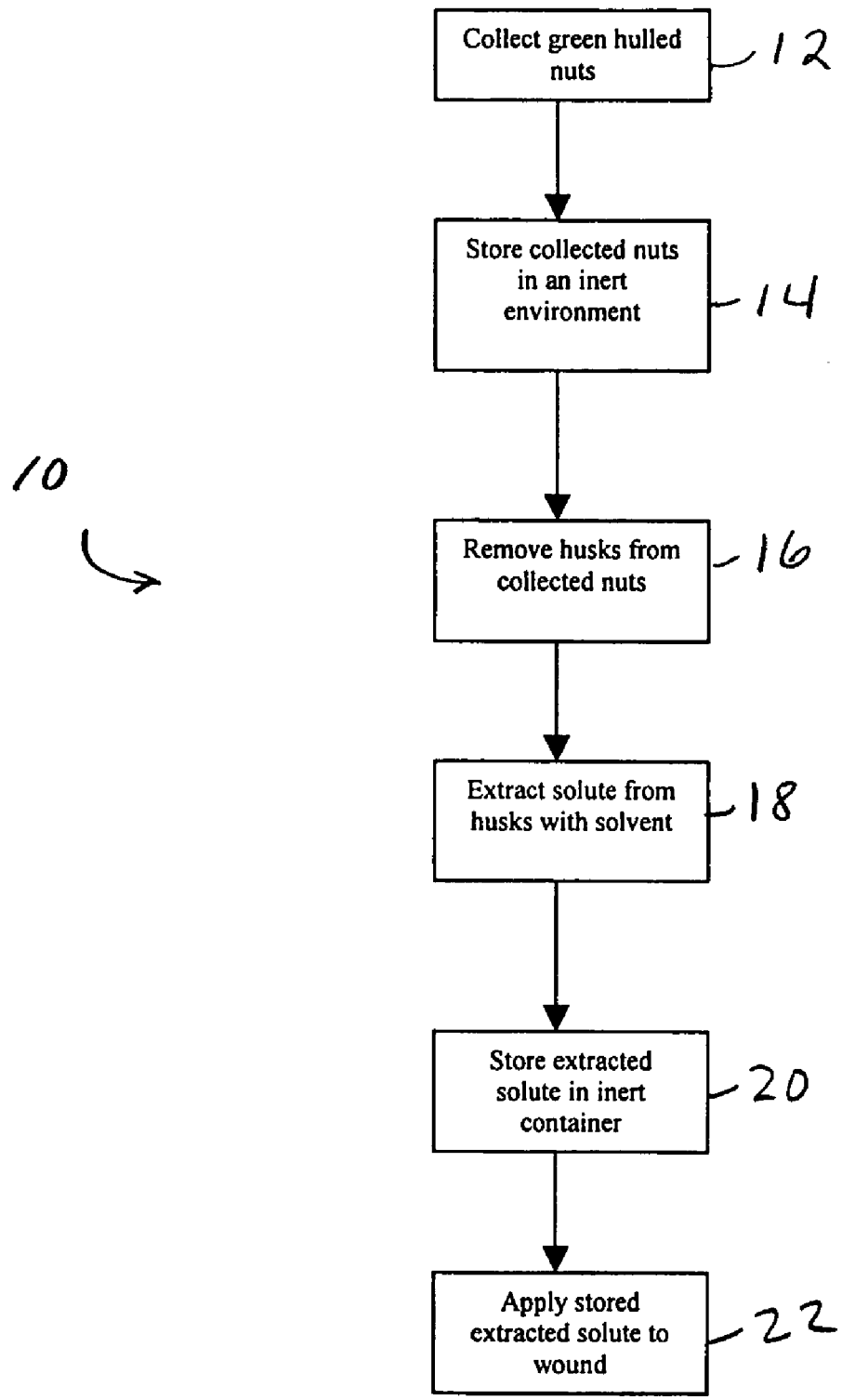
FIG. 1 illustrates a step-by-step method of the present invention.

With reference to the drawing herein, one embodiment of a method of producing and using a pathogen shield is shown in FIG. 1. The embodiment of the method 10 of FIG. 1 includes a step 12 of harvesting a quantity of nut husks for processing. The nuts can be harvested any time after the interior shell is formed. Or the nuts may be harvested as soon as dehiscence occurs. That is when the green husks or shucks have become free of the interior nutshell. Harvesting after the husks or shucks have begun to turn black is too late. Nuts considered in this process, include those from the Juglandaceae family, such as pecan, black walnut, and English walnut, and combinations of these, to name but a few. Orchard managers sometimes shake the trees in late July to reduce the number of pecans on the tree. This enables the remaining nuts to grow larger. Water extraction would be a way to utilize these early pecans.

As seen in step 14, after the nuts have been collected they should be placed into a container (not shown) having inert space that has been purged of oxygen. Examples of an inert space include a glove bag inflated with pure argon gas to displace all air from the bag. The ambient air that would typically be within the inert space is replaced with an inert gas such as nitrogen, argon, carbon dioxide, or helium or combinations there of. The gas used can be heavier than air (i.e. argon or carbon dioxide) thus slowly adding the gas to the bottom of the container can displace the air within the container. When substantially all of the oxygen has been removed or displaced from the inert space. (step 16). Removing the husks can be done manually or by using a "shuck brush" as is currently used by commercial orchards. The husks should be green during this step to ensure sufficient active solute exists within the husks. It is immaterial if the husks are still on the nut. When the husks become dry and black nothing can be extracted.

After being removed from the rest of the raw nut, the husks are collected in a vessel and soaked in a solvent, such as water. If ethanol were used the product would be a 'tincture'. During the soaking step, solute from the nut husk is extracted into the solvent thereby creating a pathogen shield elixir. It is within this elixir that the active solute or wound healing compound exists. It is important that during the extraction step the elixir be protected from oxygen. Sealing the vessel as well as subjecting the vessel to an inert gas blanket, can protect the elixir from the degrading effects of oxygen. When desired to cease solute extraction, the elixir can be separated from the husks and placed in interim storage or into containers for subsequent use. Also, many pecans were harvested in early August when large limbs broke, these yielded good quantities of the active solute. If another solvent is used, other than those listed above, it must be miscible with water because the active antiseptic is highly soluble in water and exists within the shuck as an aqueous solution. Other solvents include acetone and methyl-ethyl-ketone.

Typically, some fermentation will occur during the extraction step that produces an off-gas such as carbon dioxide, thus a positive pressure vent can be added to the container to prevent a pressure build up within the vessel. Monitoring and dealing with the fermentation not only can prevent overpressure of the vessel, it can also signal when an appropriate time to separate the husks from the resulting elixir and thus end the extraction process.

Optionally, the husks may be pressed at a pressure sufficient to extract the fluid naturally present within the nut husk. This can be done in lieu of extracting the solute with a solvent, in combination with the soaking step, or after soaking. After soaking the shucks are nearly devoid of the active solute. Preferably the pressure applied while pressing the husks is around 5000 pounds per square inch. Following the pressing function the fluid within the green husk is stored for later use or in an interim storage prior to the final packaging of the extracted fluid. Whether the fluid is stored in an interim container or in its final package, both the container and the package must be substantially free of oxygen.

Final packaging of the extracted fluid can involve storing the extracted fluid within bottles, sealed packets, or capsules. With respect to storing the extracted fluid 30 for long term storage and use, one manner provided herein involves placing it within a bottle 24. The bottle can be sealed with a foil or foil like membrane (not shown) adhered to the opening of the bottle 24. Additionally, a removable cap 26 can be provided along with the bottle 24 thereby providing a barrier seal on the bottle 24 that can further prevent exposure of the extracted fluid 30 to ambient air and other sources of oxygen. While the bottle 24 can be any size, one optional size is one that would accommodate approximately 2-4 ml of extracted liquid 30. Optionally, 30 ml glass bottles with screw top with a tin-foil lined cap can be used, up to larger bottles having a capacity in excess of four liters.

Figures 2, 3, 4:
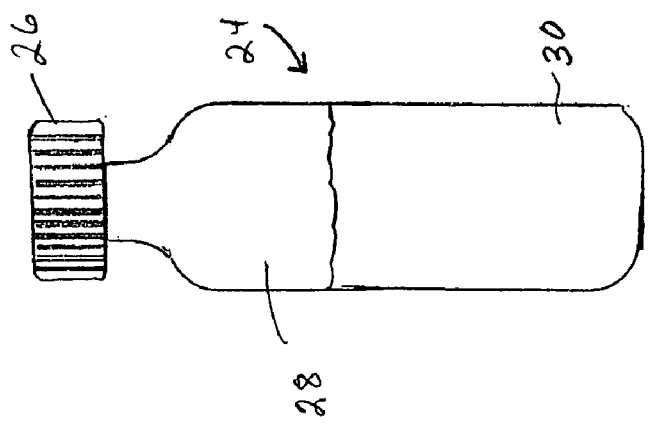
FIG. 2 depicts a side view of extracted liquid stored within a bottle.
FIG. 3 portrays in side view a packet container.
FIG. 4 shows an overhead view of a gauze patch.

With reference now to FIG. 3, an embodiment of a packet 32 of the present invention is illustrated. As shown the packet 32 is comprised of a pair of largely rectangular sides joined at their outer periphery, optionally the sides could be other shapes, such as circular or elliptical. An amount of the extracted fluid is stored within the packet 32 in an airtight environment. The packet 32 should be openable either by hand, but can also be opened with scissors or some other cutting instrument. The material of the packet 32 can be foil, plastic, a thermoplastic material, a polymeric material, or any other material that provides an atmospheric barrier (or any material that will not be permeable to oxygen), is sealable, and can be opened without undue effort. Optionally gauze 34 can be included within the packet 32, where the gauze 34 is wetted with the extracted liquid 30 prior to being stored within the packet 32. Preferably the gauze 34 is comprised of a sterile cotton or cotton like material, but can be made of any material capable of withholding a sufficient amount of extracted liquid 30 within its fibers for later application to a wound. Selection and use of an appropriate bottle 24, cap 26, packet 32, and gauze 34 is well within the capabilities of one of ordinary skill in the art.

In use, the extracted liquid 30 is applied to a wound 36 and to the skin area surrounding the wound 36. While the wound 36 of FIG. 5 is shown on a human digit 37, a wound 36 located on any part of a body can be treated with the liquid of the present invention. As shown, the extracted liquid 30 has been applied to the tip 38 of a cotton swab 40 for application onto the wound 36. However the wound 36 could be treated with the wetted gauze 34 of FIG. 4, where the gauze 34 had been wetted with the extracted fluid 30 from the bottle 24, stored within the packet 32, or wetted with the extracted fluid 30 straight from the press.

EXAMPLE 1

In one non-limiting example of the present method, nut husks were collected and then transferred to a 55-gallon drum and covered with a water solvent. The drum was sealed with a pressure relieving vent. The husk/solvent mixture was left at ambient conditions for a period of 4 days. During this time fermentation gases were produced and vented to atmosphere. Towards the end of the four-day period fermentation was vastly diminished. The resulting elixir produced by the extraction process was then drawn from the drum and stored.

EXAMPLE 2

In a non-limiting example of a method herein described, a 76 year old human subject sustained an injury involving damaged skin on his right shin about three inches above the ankle. The injury included superficial skin damage and slight bleeding. The extracted liquid of the present invention was immediately applied after the injury. A second application of the liquid was applied approximately an hour after the first application. Until the next day, the subject avoided wetting the injury. Sixteen days later the injury was completely healed within any additional intervention. Additionally, at no time did the wound become infected or exhibit an infectious appearance. It is believed that adsorption of the extracted liquid onto the skin protected against infection during the subject's healing process. The subject applied the extracted liquid on four separate occasions, to four separate wounds with the same result; namely none of the wounded areas became infected and hence all healed without complications and in a timely fashion.

Testing indicates that the expressed liquid is toxic to certain cells. The implication of this is that a long lasting protective action of the extracted liquid arises from a barrier created by adsorption of the extracted liquid on the critical cell surface membrane. Thus it has been concluded that application of the expressed liquid onto a wound provides a prophylactic effect onto the wound and protects the wound against pathogens being introduced onto the wound. Protecting a wound against such pathogens can in turn prevent infection of the wound and speed the healing of the wound.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of obtaining a pathogen shield comprising:

collecting nuts having green husks, wherein the nuts are selected from the list consisting of pecan and walnut;

storing the nuts in an inert environment substantially free of oxygen;

removing the husks from the nuts in the inert environment;

soaking the husks in a solvent thereby producing an elixir comprising a pathogen shield extracted from the husks by the solvent;

maintaining the husks and solvent in an inert and a substantially oxygen free environment;

separating the husks from the elixir; and storing the elixir comprising the pathogen shield therein for later use.

2. The method of claim 1 wherein said solvent is selected from the list consisting of water, acetone, ethanol, and isopropyl alcohol.

3. The method of claim 1 wherein the step of storing the elixir comprises storing the elixir in a sealed inert environment.

4. The method of claim 1, wherein the husks are soaked for a period of about 3 days to 5 days.

* * * * *